(12) United States Patent
Audoglio

(10) Patent No.: US 6,549,813 B2
(45) Date of Patent: Apr. 15, 2003

(54) TWO-CHAMBER SINGLE-PASS ELECTRODE ARRANGEMENT

(75) Inventor: Roberto Audoglio, Linarolo (IT)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 228 days.

(21) Appl. No.: 09/740,259
(22) Filed: Dec. 18, 2000

(65) Prior Publication Data
US 2001/0012958 A1 Aug. 9, 2001

(30) Foreign Application Priority Data
Dec. 23, 1999 (DE) .......................... 199 63 602

(51) Int. Cl.$^7$ ................................ A61N 1/05
(52) U.S. Cl. ................. 607/123; 607/119; 607/126
(58) Field of Search ................. 607/119, 122, 607/123, 125, 126–128

(56) References Cited

U.S. PATENT DOCUMENTS

| | | | |
|---|---|---|---|
| 4,458,677 A | * | 7/1984 | McCorkle, Jr. ............ 607/123 |
| 4,479,500 A | * | 10/1984 | Smits ...................... 607/123 |
| 5,628,779 A | | 5/1997 | Bornzin |
| 5,755,766 A | | 5/1998 | Chastain |
| 6,006,137 A | | 12/1999 | Williams |

FOREIGN PATENT DOCUMENTS

| | | |
|---|---|---|
| EP | 0 788 808 A2 | 8/1997 |
| WO | WO 83/04181 A1 | 12/1983 |
| WO | WO 97/36639 A1 | 10/1997 |
| WO | WO 99/45999 A1 | 9/1999 |
| WO | WO 99/55412 A1 | 11/1999 |

* cited by examiner

Primary Examiner—J. Casimer Jacyna
(74) Attorney, Agent, or Firm—Hahn Loeser + Parks LLP; Stephen L. Grant

(57) ABSTRACT

An electrode arrangement (10) comprising a first electrode cable (12) which is to be inserted into the coronary sinus and which has an electrode conductor (32) and at least one electrode (38, 40) for outputting and/or receiving electrical signals in the coronary sinus. Longitudinally slidably guidable in the lumen of the first electrode cable (12) at least in a longitudinal portion-wise manner is a second electrode cable (14) which can issue from the first electrode cable through an opening (52) at the distal end thereof and which is adapted for insertion into a cardiac vein which opens into the coronary sinus.

60 Claims, 1 Drawing Sheet

TWO-CHAMBER SINGLE-PASS ELECTRODE ARRANGEMENT

The invention concerns an electrode arrangement comprising a first electrode cable which is to be inserted into the coronary sinus and which has an electrode conductor and at least one electrode for outputting and/or receiving electrical signals in the coronary sinus.

BACKGROUND OF THE ART

Heart stimulation by way of the coronary sinus (CS) is nowadays a form of therapy which is used only rarely. The cause of this, besides difficulties in positioning the electrodes and the threat of complications such as perforation, is also the lack of suitable electrode arrangements.

However, situations are known in which CS-stimulation represents a preferred form of therapy, for example in regard to the implantation of anti-tachycardial pacemakers, in which the stimulation electrode is to be in the proximity of the re-entry circuit. Stimulation of the left-hand half of the heart by way of the CS and a cardiac vein is also conceivable.

Therefore the object of the invention is to provide an electrode arrangement for electrical cardiac therapy.

SUMMARY OF THE INVENTION

That object is attained by an electrode arrangement having the features of claim 1.

In accordance with the invention, longitudinally slidably guidable in the lumen of the first electrode cable at least in a longitudinal portion-wise manner is a second electrode cable which can issue from the first electrode cable through an opening at the distal end thereof and which is adapted for insertion into a cardiac vein which opens into the coronary sinus.

The electrode arrangement according to the invention is designed primarily for stimulation of the left-hand half of the heart by way of the coronary sinus (CS) and a left-hand cardiac vein. The design configuration thereof permits relatively easy insertion of the electrodes into the vessels. Only one vessel incision is required for the insertion of both electrode cables, for example in the Vena cephalica or the Vena subclavia or other vessels. In that respect, firstly the first electrode cable can be inserted and placed in the coronary sinus. Then, the second electrode cable can be passed through the lumen of the first electrode cable and, issuing from the distal end thereof, inserted into a cardiac vein.

After the step of positioning the first electrode cable its lumen can alternatively firstly be used for inserting a Swan-Ganz catheter in order to inject an X-ray contrast agent into the cardiac veins. In that way the cardiac veins can then be rendered visible by means of fluoroscopy. That procedure facilitates the subsequently necessary operation of precisely positioning the second electrode cable in the cardiac vein.

Alternatively however the second electrode cable can also already be introduced, upon insertion of the first electrode cable, as far as the distal opening thereof.

The electrode of the first electrode cable is preferably in the form of a ring electrode. In a preferred embodiment of the invention, the first electrode cable has two axially spaced ring electrodes which can be positioned in the CS. They are preferably insulated relative to each other and can be polarized in opposite relationship.

Fixing of the first electrode cable in the coronary sinus can be effected both actively and also passively, in which respect care is to be taken to ensure that the anchoring device involves an only minimal congestion or flow-stemming effect. For example an anchoring device can be in the form of a helical screwthread portion comprising a flexible plastic material and can be arranged on the outer sheathing of the first electrode cable in the region of its distal end. Fixing is also conceivable by means of fins of elastic plastic material, which are of a dimension corresponding to the CS and which are inclined towards the proximal end. In order to reduce the flow resistance of such a fixing device the fins may each extend only over a portion of the periphery of the sheathing and can be arranged in displaced relationship both in the axial and in the peripheral direction.

In a development of the invention the first electrode cable has an external sheathing with a receiving opening for the second electrode cable. Between the receiving opening and the distal electrode the lumen of the first electrode cable is increased to such an extent that the second electrode cable can be passed along the electrode conductor of the first electrode cable.

In a further embodiment arresting of the axial position of the second electrode cable relative to the external sheathing is possible. In that way, after the electrodes have been positioned in the CS and in the cardiac vein, the spacing of the cardiac vein electrode with respect to the CS-electrode or electrodes is prevented from altering.

The arresting action is preferably achieved by means of a clamping device at the receiving opening, for example with an eccentric screw which extends in the lumen of the external sheathing perpendicularly to the longitudinal axis between the first and second electrode lines.

For that purpose the cross-sectional profile of the external sheathing is widened at the receiving opening. At the same time that makes it easier to introduce the second electrode cable.

A seal at the distal opening of the first electrode cable prevents fluid from passing into the lumen of the external sheathing. The lumen is preferably also sealed off as long as the second electrode cable has not yet been inserted into the cardiac vein.

In a further embodiment the second electrode cable tapers towards its distal end in order to form a low level of flow resistance.

Preferably a tip electrode at the distal end of the second electrode cable is used for stimulation of the left ventricle. However, it is in principle also possible to use electrode arrangements with one or more ring electrodes in the portion of the second electrode cable, which projects in a distal direction out of the external sheathing of the first electrode cable.

A further embodiment provides a device for fixing the second electrode cable in the cardiac vein. With suitable dimensioning, it can be of a similar configuration to the fixing device for the CS.

An extension with at least one marker can be arranged at the distal end of the second electrode cable. The marker can be located by means of an imaging process from outside the body. For example, the marker includes a material or is made completely from a material with which a contrast in relation to body-specific materials can be produced in an image produced by the imaging process. The marker for example may contain gold for X-ray irradiation of the patient for monitoring the procedure for inserting the electrodes. One or more such markers may also be provided in the distal end region of the first electrode cable.

The extension is made from flexible material and in particular can be adapted to be controllable, for example insofar as the guide wire for the second electrode cable can be introduced thereinto. It is however also possible to conceive of a design configuration in which the extension is substantially J-shaped or horn-shaped and upon being advanced in the vessels is guided by rotation of the second electrode cable.

To achieve a high level of breaking strength the electrode conductor of the first electrode cable is of a two-coil configuration. In an embodiment with two CS-electrodes, two respectively electrically insulated wires extend in each of the two coils of the electrode conductor.

In a further embodiment, a respective guide wire can be introduced into the lumen of the first and the second electrode conductors, for insertion and positioning of the electrode cable.

In order to provide sufficient clearance in regard to positioning of the second electrode cable and in regard to establishing the spacing between the cardiac vein electrode and the CS-electrodes, the second electrode cable can extend in the form of an annular loop, between its proximal end and the entry into the receiving opening of the first electrode cable.

BRIEF DESCRIPTION OF THE DRAWINGS

Further advantageous of the invention will be clearly apparent in the description hereinafter of a preferred embodiment of the invention with reference to the drawing.

The single FIG. 1 of the drawing is a simplified, partly sectional view of an electrode arrangement for CS- and LV-stimulation.

DETAILED DESCRIPTION OF THE INVENTION

Figure 1:
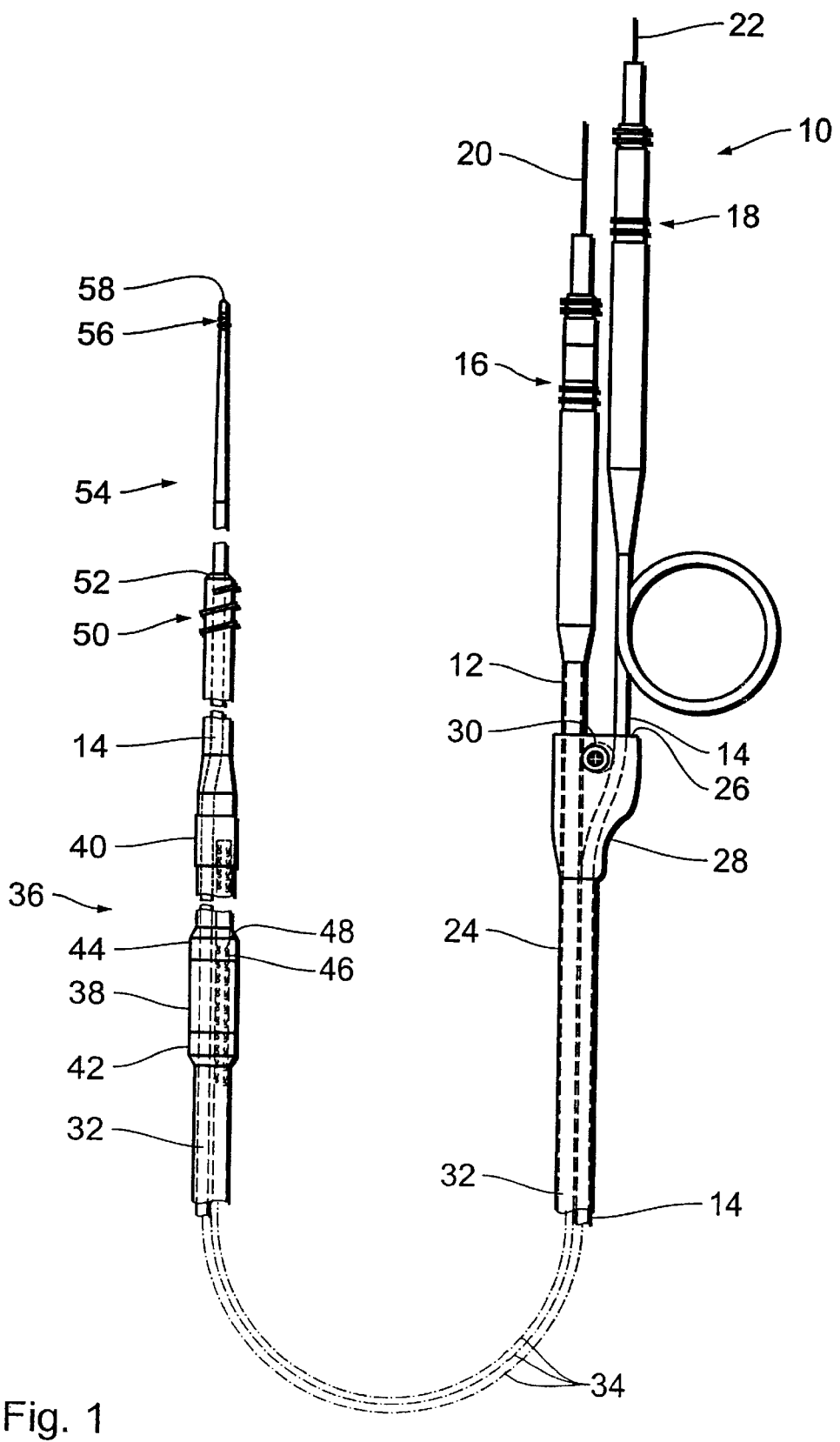

The electrode arrangement 10 serves for stimulation of the left atrium by way of the coronary sinus and for stimulation of the left ventricle by way of a cardiac vein which opens into the coronary sinus, and for that purpose it has two electrode cables (pacemaker probes) 12 and 14. At its proximal end the first electrode cable 12 can be connected by means of a bipolar IS-1 plug to a pacemaker (not shown). For that purpose, at its proximal end, the second electrode cable 14 has a unipolar IS-1 plug.

The proximal end faces of the plugs 16 and 18 each have a respective central opening for the insertion of a guide wire (mandrel) 20 and 22 respectively. The guide wires 20 and 22 can be passed from the plugs 16 and 18 in the lumens of the electrode cables 12 and 14 to the respective distal ends thereof. Both electrode cables can be advanced from an incision point into their definitive position, by means of the controllable guide wires 20 and 22.

In a longitudinal portion which extends from beyond the plug 16 to the distal end of the first electrode cable 12 the first electrode cable 12 has an external sheathing 24. The lumen thereof accommodates on the one hand the first electrode cable 12 itself and on the other hand permits the second electrode cable 14 to pass therethrough. The second electrode cable 14 can be introduced at an opening 26 into a receiving portion 28 of the external sheathing 24. The electrode arrangement of the present embodiment is therefore a so-called "Single Pass Dual Lead" arrangement.

The receiving portion 28 is increased in width from a distal location towards the opening 26 and has a substantially centrally arranged arresting screw 30 which extends transversely through the lumen between the first and second electrode cables. The arresting screw 30 is an eccentric screw and can be turned into a position in which it presses the second electrode cable 14 against the inside wall of the receiving portion 28 and thereby clamps it between itself and the inside wall.

Adjoining the receiving portion 28 in a distal direction is a portion of the first electrode cable 12, of uniform cross-section. The first and second electrode cables 12 and 14 extend in mutually juxtaposed relationship in the lumen of the external sheathing 24. The external sheathing and the sheaths of the first electrode conductor 32 and the second electrode cable 14 which are guided therein are made from low-friction materials so that, upon insertion of the second electrode cable 14, only low axial forces occur and dislocation of the electrodes which are described in greater detail hereinafter is avoided.

FIG. 1 does not show the entire length of the electrode arrangement 10. Arcuate broken lines 34 symbolically represent the continuation of the portion of the first electrode cable 12 of uniform cross-section to the distal portion 36, described hereinafter, of the electrode arrangement 10.

Provided in the distal portion 36 are two axially spaced, annular CS-electrodes 38 and 40 which enclose the outer sheathing 24. The axial extent of the proximal ring electrode 38 is somewhat greater than that of the distal ring electrode 40. In the region of the axial extent of the ring electrodes 38 and 40 the lumen of the external sheathing 24 is sealed off to prevent the ingress of fluid and electrically insulated. For that purpose the proximal ring electrode 40 is positioned in an axial direction between two insulating rings 42 and 44.

The electrical power supply to the ring electrodes 38 and 40 is effected by means of the electrode conductor 32 which is of a two-coil nature. Both conductor coils 46 and 48 (shown here in section) contain two respective electrically insulated wires (not shown) and are wound in mutually juxtaposed relationship. The wires are coated with PFE for electrical insulation purposes.

The first electrode conductor 34 terminates in the region of the distal ring electrode 40. From here the external sheathing 24 of the first electrode cable 12 tapers in the distal direction. Only the second electrode cable 14 is still guided in the lumen thereof.

Arranged at the distal end of the first electrode cable 12 is a CS-fixing device 50 in the form of a helical screwthread portion with two and a half turns.

The distal tip of the first electrode cable 12 is protected against the ingress of fluid by means of a seal 52 which has two O-rings. The seal permits the distal end 54 of the second electrode cable to be taken out of the lumen of the external sheathing 24 of the first electrode cable 12. As described in greater detail hereinbefore, before the insertion of the tip electrode 58 firstly a Swan-Ganz catheter can be passed through the lumen of the external sheathing 24 in order to inject an X-ray contrast agent into the cardiac veins. The Swan-Ganz catheter is then withdrawn, in which case the seal 52 at the distal end 52 of the first electrode cable is closed again.

The second electrode cable 14 tapers in the portion 54 to its distal end at which are arranged a fixing device 56 and a hemispherical tip electrode 58. In this embodiment the fixing device 56 is also in the form of a helical screwthread portion.

Other embodiments of the invention from that described herein can also be envisaged. Thus the second electrode cable can also be of a bipolar nature. In principle a unipolar or a bipolar structure for the first and/or the second electrode cable is possible.

The second electrode cable can be of a two-coil nature like the first in the embodiment described in detail hereinbefore.

What is claimed is:

1. An electrode arrangement for insertion into a coronary sinus and a cardiac vein of a user, the coronary vein opening into the coronary sinus, the arrangement comprising:
   an external sheathing having a distal end and a lumen;
   a first electrode cable in the lumen, having an electrode conductor and at least one electrode for outputting and/or receiving electrical signals in the coronary sinus; and
   a second electrode cable in the lumen and slidably guidable therein, in at least a longitudinal portion-wise manner, the second electrode cable being able to issue from an opening at the distal end thereof and which is adapted for insertion into the cardiac vein, the second electrode cable tapering towards the distal end.

2. The electrode arrangement as set forth in claim 1 characterized in that at least one said at least one electrode is a ring electrode.

3. The electrode arrangement of claim 2 wherein the first electrode cable has two axially spaced electrodes.

4. The electrode arrangement as set forth in claim 3 wherein the two electrodes are electrically insulated from each other and are oppositely polarizable.

5. The electrode arrangement of claim 1 wherein the first electrode cable has two axially spaced electrodes.

6. The electrode arrangement as set forth in claim 5 characterized in that the two electrodes are electrically insulated from each other and are oppositely polarizable.

7. The electrode arrangement of claim 5, wherein the first of the two axially-spaced electrodes is a proximal electrode and the second electrode is a distal electrode.

8. The electrode arrangement of claim 7 wherein the external sheathing tapers in a direction distal to the distal electrode.

9. The electrode arrangement of claim 1 wherein the external sheathing has a device for fixing in the coronary sinus.

10. The electrode arrangement of claim 1 wherein the external sheathing has a receiving opening for the second electrode cable.

11. The electrode arrangement of claim 10 wherein there is a means for arresting the axial position of the second electrode cable relative to the external sheathing.

12. The electrode arrangement as set forth in claim 11 wherein the arresting means comprises a clamping device.

13. The electrode arrangement as set forth in claim 12 wherein the clamping device is provided at the receiving opening and has an eccentric screw which extends in the lumen of the external sheathing perpendicularly to the longitudinal axis thereof between the first and the second electrode cables.

14. The electrode arrangement as set forth in claim 13 wherein the external sheathing has a cross-sectional profile which increases in width towards the receiving opening.

15. The electrode arrangement of claim 10 wherein the second electrode cable extends in the form of an annular loop between a proximal end thereof and the entry into the receiving opening.

16. The electrode arrangement of claim 1 wherein the lumen of the external sheathing is electrically insulated and sealed in relation to entry and exit of fluid in the region of the at least one electrode.

17. The electrode arrangement as set forth in claim 16 characterized by a seal to prevent the ingress of fluid at the distal opening of the external sheathing.

18. The electrode arrangement of claim 1 wherein the distal end of the second electrode cable comprises a tip electrode.

19. The electrode arrangement of claim 1 wherein the distal end of the second electrode cable comprises at least one ring electrode.

20. The electrode arrangement of claim 1 wherein the distal end of the second electrode cable comprises a device for fixing the second electrode cable in the cardiac vein.

21. The electrode arrangement of claim 1 wherein the second electrode cable comprises a bipolar design.

22. The electrode arrangement of claim 1 wherein the electrode conductor of the first electrode cable is of a two-coil nature.

23. The electrode arrangement as set forth in claim 22 characterized in that two respectively electrically insulated wires extend in each of the two coils of the electrode conductor.

24. The electrode arrangement of claim 1 wherein the first and second electrode cables each have a lumen for insertion of a guide wire therein.

25. An electrode arrangement for insertion into a coronary sinus and a cardiac vein of a user, the coronary vein opening into the coronary sinus, the arrangement comprising:
   an external sheathing having a distal end and a lumen;
   a first electrode cable in the lumen, having an electrode conductor of a two-coil nature, wherein two respectively electrically insulated wires extend in each of the two coils of the electrode conductor, and at least one electrode for outputting and/or receiving electrical signals in the coronary sinus; and
   a second electrode cable in the lumen and slidably guidable therein, in at least a longitudinal portion-wise manner, the second electrode cable being able to issue from an opening at the distal end thereof and which is adapted for insertion into the cardiac vein.

26. The electrode arrangement as set forth in claim 25 characterized in that at least one said at least one electrode is a ring electrode.

27. The electrode arrangement of claim 26 wherein the first electrode cable has two axially spaced electrodes.

28. The electrode arrangement as set forth in claim 27 wherein the two electrodes are electrically insulated from each other and are oppositely polarizable.

29. The electrode arrangement of claim 25 wherein the first electrode cable has two axially spaced electrodes.

30. The electrode arrangement as set forth in claim 29 characterized in that the two electrodes are electrically insulated from each other and are oppositely polarizable.

31. The electrode arrangement of claim 29 wherein the first of the two axially-spaced electrodes is a proximal electrode and the second electrode is a distal electrode.

32. The electrode arrangement of claim 31 wherein the external sheathing tapers in a direction distal to the distal electrode.

33. The electrode arrangement of claim 25 wherein the external sheathing has a device for fixing in the coronary sinus.

34. The electrode arrangement of claim 25 wherein the external sheathing has a receiving opening for the second electrode cable.

35. The electrode arrangement of claim 34 wherein there is a means for arresting the axial position of the second electrode cable relative to the external sheathing.

36. The electrode arrangement as set forth in claim 35 wherein the arresting means comprises a clamping device.

37. The electrode arrangement as set forth in claim 36 wherein the clamping device is provided at the receiving opening and has an eccentric screw which extends in the lumen of the external sheathing perpendicularly to the longitudinal axis thereof between the first and the second electrode cables.

38. The electrode arrangement as set forth in claim 37 wherein the external sheathing has a cross-sectional profile which increases in width towards the receiving opening.

39. The electrode arrangement of claim 25 wherein the lumen of the external sheathing is electrically insulated and sealed in relation to entry and exit of fluid in the region of the at least one electrode.

40. The electrode arrangement as set forth in claim 39 characterized by a seal to prevent the ingress of fluid at the distal opening of the external sheathing.

41. The electrode arrangement of claim 25 wherein the second electrode cable comprises a bipolar design.

42. The electrode arrangement of claim 25 wherein the first and second electrode cables each have a lumen for insertion of a guide wire therein.

43. The electrode arrangement of claim 25 wherein the second electrode cable tapers towards a distal end thereof, the distal end comprising a tip electrode.

44. The electrode arrangement of claim 25 wherein the second electrode cable tapers towards a distal end thereof the distal end comprising at least one ring electrode.

45. The electrode arrangement of claim 25 wherein the second electrode cable tapers towards a distal end thereof, the distal end comprising a device for fixing the second electrode cable in the cardiac vein.

46. An electrode arrangement for insertion into a coronary sinus and a cardiac vein of a user, the coronary vein opening into the coronary sinus, the arrangement comprising:

an external sheathing having a distal end and a lumen;

a first electrode cable in the lumen, having an electrode conductor and at least one electrode for outputting and/or receiving electrical signals in the coronary sinus; and a second electrode cable in the lumen and slidably guidable therein, in at least a longitudinal portion-wise manner, the second electrode cable being able to issue from an opening at the distal end thereof and which is adapted for insertion into the cardiac vein;

wherein the external sheathing has a receiving opening for the second electrode cable, with a clamping device for arresting the axial position of the second electrode cable relative to the external sheathing, the clamping device provided at the receiving opening and having an eccentric screw which extends in the lumen of the external sheathing perpendicularly to the longitudinal axis thereof between the first and the second electrode cables.

47. The electrode arrangement as set forth in claim 46 characterized in that at least one said at least one electrode is a ring electrode.

48. The electrode arrangement of claim 47 wherein the first electrode cable has two axially spaced electrodes.

49. The electrode arrangement as set forth in claim 48 wherein the two electrodes are electrically insulated from each other and are oppositely polarizable.

50. The electrode arrangement of claim 46 wherein the first electrode cable has two axially spaced electrodes.

51. The electrode arrangement as set forth in claim 50 characterized in that the two electrodes are electrically insulated from each other and are oppositely polarizable.

52. The electrode arrangement of claim 50 wherein the first of the two axially-spaced electrodes is a proximal electrode and the second electrode is a distal electrode.

53. The electrode arrangement of claim 52 wherein the external sheathing tapers in a direction distal to the distal electrode.

54. The electrode arrangement of claim 46 wherein the external sheathing has a device for fixing in the coronary sinus.

55. The electrode arrangement of claim 46 wherein the second electrode cable extends in the form of an annular loop between a proximal end thereof and the entry into the receiving opening.

56. The electrode arrangement as set forth in claim 46 wherein the external sheathing has a cross-sectional profile which increases in width towards the receiving opening.

57. The electrode arrangement of claim 46 wherein the lumen of the external sheathing is electrically insulated and sealed in relation to entry and exit of fluid in the region of the at least one electrode.

58. The electrode arrangement as set forth in claim 57 characterized by a seal to prevent the ingress of fluid at the distal opening of the external sheathing.

59. The electrode arrangement of claim 46 wherein the second electrode cable comprises a bipolar design.

60. The electrode arrangement of claim 46 wherein the first and second electrode cables each have a lumen for insertion of a guide wire therein.

* * * * *